(12) United States Patent
Kanayama et al.

(10) Patent No.: US 6,680,411 B2
(45) Date of Patent: Jan. 20, 2004

(54) CARBORANE SUPERCLUSTER AND METHOD OF PRODUCING SAME

(75) Inventors: Toshihiko Kanayama, Ibaraki (JP); Hidefumi Hiura, Tokyo (JP)

(73) Assignees: Agency of Industrial Science and Technology, Tokyo (JP); T shihiko Kanayama, Ibaraki (JP); NEC Corporation, Tokyo (JP)

( * ) Notice: Subject to any disclaimer, the term of this patent is extended or adjusted under 35 U.S.C. 154(b) by 0 days.

(21) Appl. No.: 10/152,730

(22) Filed: May 23, 2002

(65) Prior Publication Data

US 2003/0023118 A1 Jan. 30, 2003

(30) Foreign Application Priority Data

May 23, 2001 (JP) ........................................ 2001-153670

(51) Int. Cl.$^7$ .................................................. C07F 5/02
(52) U.S. Cl. ............................................................ 568/4
(58) Field of Search .......................................... 568/3, 4

(56) References Cited

U.S. PATENT DOCUMENTS 6,423,199 B1 * 7/2002 Tinker et al. ................ 204/536

OTHER PUBLICATIONS

CA:85:200492 abs of J Inorg Nucl Chem by Mathur et al 38(9) pp 1597–1600 1976.*
CA:118:124699 abs of JACS by Yang et al 115(1) pp 193–5 1993.*
CA:112:55979 abs of Metalloorgnicheskaya Khimiya by Usiatinskii et al 1(6) pp 1420–3 1988.*
CA:124:261111 abs of Inorganica Chimica Acta by Yang et al 240(1–2) pp 371–8 1995.*
CA:85:200492 abs of J Inorg Nucl. Chem by Mathur et al 38(9) pp 1597–1600 1976.*
CA:87:135498 abs of Zh Obshch Khim by Zakharkin et al 47(4) pp 963–4 1977.*

* cited by examiner

Primary Examiner—Jean F. Vollano
(74) Attorney, Agent, or Firm—Young & Thompson

(57) ABSTRACT

A carborane supercluster consisting of carborane ($C_2B_{10}H_{12}$) as its constituent unit expressed as a molecular formula $C_{2m}B_{10m}H_{12m-x}$, where x is a positive integer (i.e., x=1, 2, 3, . . . ) and m is an integer greater than unity (i.e., m=2, 3, . . . ). The parameter x represents the count of removed or detached hydrogen atoms. The parameter a represents the count of the clusters linked together. To produce the supercluster, carborane ($C_2B_{10}H_{12}$) is ionized in a reaction chamber to generate carborane ions and then, the carborane ions thus generated are successively reacted with the remaining neutral (i.e., non-ionized) carborane ($C_2B_{10}H_{12}$), thereby generating the carborane supercluster. Preferably, the cluster of the carborane consists of at least two of o-carborane, m-carborane, and p-carborane.

18 Claims, 9 Drawing Sheets

FIG. 1
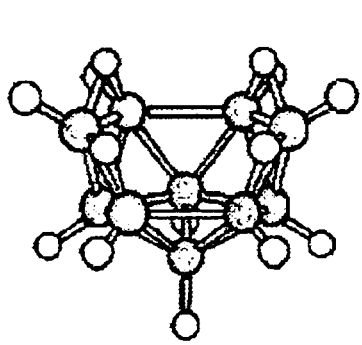
(a) decarborane (14)
($B_{10}H_{14}$)
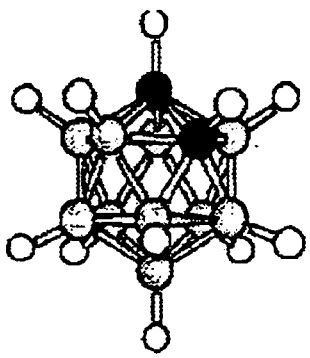
(b) o-carborane
($B_{10}C_2H_{12}$)
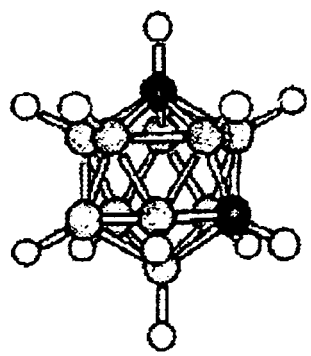
(c) m-carborane
($B_{10}C_2H_{12}$)
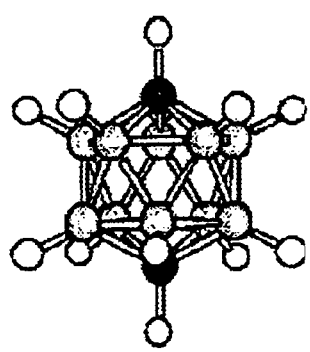
(d) p-carborane
($B_{10}C_2H_{12}$)
○ hydrogen (H)
◉ boron (B)
● carbon (C)

ONE-DIMENSIONAL CHAIN LINK

THREE-DIMENSIONAL CLOSE-PACKED LINK

CARBORANE SUPERCLUSTER AND METHOD OF PRODUCING SAME

BACKGROUND OF THE INVENTION

1. Field of the Invention

The present invention relates to a carborane supercluster and a method of producing the same. More particularly, the invention relates to a carborane supercluster containing boron-rich carborane (if carborane is given as the molecular formula $C_2B_{10}H_{12}$, the boron content is approximately 75% by weight) with high thermodynamic and chemical stability as its unit constituent (i.e., a cluster molecule), and a method of producing the same.

2. Description of the Related Art

Carborane is generally a compound consisting of boron hydride into which carbon atoms are introduced which has a hollow-cage-shaped structure. Boron hydride (i.e., hydride of boron) is usually termed "borane", because of its similarity to "alkane" (i.e., saturated hydrocarbons).

A well-known borane is decaborane (14) expressed by a chemical formula $B_{10}H_{14}$, which is comparatively stable and industrially important. Decaborane (14) has a skeletal structure of boron (B) atoms, as shown in FIG. 1(a). The skeletal boron structure of FIG. 1(a), which is cage-shaped, constitutes a regular icosahedron formed by 12 boron atoms located at its respective vertexes and at the same time, the two adjacent boron atoms are removed therefrom. The molecular structure of decaborane (14) is that the remaining ten boron atoms of the skeletal structure are respectively terminated by hydrogen (H) atoms, where the two adjacent boron atoms including opened sites are bridged by hydrogen atoms at four positions.

o-Carborane (i.e., ortho-carborane, 1,2-dicarba-closo-dodecaborane), which is expressed by a chemical formula $C_2B_{10}H_{12}$, is known as one of typical carboranes. o-Carborane has a similar molecular structure to the above-described molecular structure of decaborane (14), as shown in FIG. 1(b). Specifically, the four bridging hydrogen atoms are removed from the above-described molecular structure of decaborane (14) and then, two carbon atoms are respectively inserted to the two opened sites thereof, thereby completing the regular icosahedron. Moreover, the two carbon atoms and the ten boron atoms, which are respectively located at the 12 vertexes of the icosahedron, are respectively terminated by hydrogen atoms. Thus, the molecular structure of o-carborane is formed.

Actually, o-carborane is synthesized from decaborane (14). Specifically, if decaborane (14) is reacted with acetylene under the existence of a Lewis base such as acetonitrile and alkylamines, o-carborane is produced. o-Carborane has two isomers, m-carborane (i.e., meta-carborane, 1,7-dicarba-closo-dodecaborane) and p-carborane (i.e., para-carborane, 1,12-dicarba-closo-dodecaborane), according to the relative position of the two carbon atoms. m-Carborane has a molecular structure shown in FIG. 1(c), where one boron atom is located between the two carbon atoms. p-Carborane has a molecular structure shown in FIG. 1(d), where the two carbon atoms are located symmetrically with respect to the center of the regular icosahedron.

If o-carborane is heated at 425° C. in an inert atmosphere, it is irreversibly isomerized to m-carborane. If o-carborane is heated at 700° C. in an inert atmosphere, it is irreversibly isomerized to 75% of m-carborane and 25% of p-carborane.

In general, a geometrically-closed, cage-shaped borane cluster (which is expressed by a chemical formula $B_nH_n$, where n is a positive integer) has (n+1) bonding molecular orbitals in its cage-shaped skeletal structure. Thus, to close electronically the shell of the borane cluster, 2(n+1) electrons are necessary to fill these orbitals.

Regarding boron, a boron atom has three valence electrons, where one of the valence electrons is used for forming the B—H bond. Therefore, the remaining two electrons are available to the formation of the skeletal structure. For example, with dodecaborane expressed as $B_{12}H_{12}$ (n=12), which is neutral and which has a skeletal structure of a regular icosahedron, 26 (=2(12+1)) electrons are necessary to fill the molecular orbitals to thereby close electronically the shell. Since dodecaborane contains 12 boron atoms 24 (=2×12) electrons are available to the formation of the skeletal structure. This means that two electrons are deficient. Accordingly, the shell of dodecaborane ($B_{12}H_{12}$) is unable to be closed electronically and thus, dodecaborane is instable.

Unlike this, with carborane ($C_2B_{10}H_{12}$), where the two boron atoms of dodecaborane ($B_{12}H_{12}$) are respectively replaced with two carbon atoms, each of these carbon atoms provides three electrons available to the formation of the skeletal structure. This is because a carbon atom has four valence electrons while one valence electron is used for forming the C—H bond. Therefore, carborane contains 26 (=2×10+3×2) electrons available to the formation of the skeletal structure. This means that the bonding orbitals of carborane are filled and thus, its shell is closed electronically. Moreover, the molecular structure of carborane is geometrically closed. Due to the synergism of the geometrically-closed molecular structure and the electronically-closed shell, carborane is expected very stable.

In the following explanation of this specification, the word "carborane" means a specific boron hydride expressed by $C_2B_{10}H_{12}$ for the sake of simplification.

Boranes, which are used as the starting source material for synthesizing a desired material, are generally instable. In contrast, the carborane ($C_2B_{10}H_{12}$) is chemically stable against reagents such as oxidizing agents, strong acids (heated, concentrated sulfuric acid and nitric acid), and alcohols. Moreover, the carborane ($C_2B_{10}H_{12}$) is not deteriorated at high temperatures, which is simply isomerized even at 700° C. as described previously. This means that the carborane ($C_2B_{10}H_{12}$) is very stable not only chemically but also thermally.

To utilize the chemical and thermal stability of the carborane, conventionally, the carborane has been introduced into a macromolecule as a function group to thereby improve the characteristic of the macromolecule. These carborane-introduced macromolecules have been used for heat- and chemical-resistant piping materials, gaskets, membranes, and covering materials.

Furthermore, to make use of the excellent insulation properties of the carborane-introduced macromolecules, insulating/insulated gloves and insulating/insulated clothes have been developed and at the same time, various trials to use the macromolecules as the integrated-circuit insulator have been made. To utilize the rigidity or inflexibility of the carborane molecules, application as constituent elements of liquid crystals has been studied as well.

Moreover, since the boron content of the carborane is approximately 75 wt %, applications that use the properties of boron (which is a trivalent element containing three valence electrons) have been developed. Boron is usually used as a dopant for introducing holes into silicon (which is a tetravalent element containing four valence electrons). Similar to this, to produce a p-type semiconductor, there has been a trial to deposit the carborane on a silicon substrate by a CVD (Chemical Vapor Deposition) process.

Boron has two stable isotopes, $^{10}B$ (19.8%) and $^{11}B$ (80.2%). The isotope $^{10}B$ has a very large cross-section ($3.840 \times 10^{-\infty} m^2$) with respect to thermal neutron capture and therefore, it has been used as a neutron capture agent. High-energy particles generated through the nuclear reaction $^{10}B+n=^{4}He+^{7}Li+2.79$ MeV (n: neutron, MeV: $10^6$ electron volts) have a property that breaks all substances existing in their flying range. An application of this property to medical care is "boron-neutron capture therapy", where a derivative of the carborane is administrated to a sufferer from a tumor to thereby enter an invaded organ and then, a neutron beam is irradiated to the tumor cells to necrotize the same.

Additionally, to utilize the nature of a complex of the carborane to capture metal ions, a research to collect radioactive ions from nuclear wastes to condense the same has been made.

Additionally, to utilize the nature of a complex of the carborane to capture metal ions, a research to collect radioactive ions from nuclear wastes to condense the same has been being made.

As described above, the carborane ($C_2B_{10}H_{12}$) is available for heat- or fire-resistance materials, chemical-resistant materials, semiconductor materials, optical materials represented by liquid crystals, neutron-capturing agents in nuclear power applications, medicaments used for boron-neutron capture therapy (which utilizes a rays generated by the neutron capture property of boron), and agents for treating radioactive wastes. Therefore, it is highly useful or valuable in various industrial fields. However, there has been no substance or material where the molecules of the carborane are directly linked and accumulated.

It is known that if a substance is physically divided into pieces, the properties will differ remarkably from those extrapolated based on the properties of a bulk solid. In general, an ultrafine substance with an atomicity of approximately $10^3$ or less is termed "cluster". A cluster contains an extremely small number of constituent atoms and thus, the properties will vary conspicuously even if the count of the constituent atoms of a cluster is different from another by one. Moreover, since the bonding pattern or form between the atoms varies according to the kind of the atoms, the properties will differ greatly. This means that various properties can be developed or expressed by controlling the size of a cluster and/or choosing the constituent atoms.

Furthermore, if a microstructure is formed by a cluster or clusters with a specific size and a specific composition, a novel property or properties is/are expected to be born. In general, the minimum constituent unit of a cluster is an atom; however, a micro-substance consisting of clusters gathered with some chemical bonds is termed "supercluster", where the cluster is the minimum constituent unit. This is because this micro-substance consists of a "cluster of the clusters". To generate such a supercluster, the cluster as the minimum constituent unit (i.e., the minimum unit cluster) needs to have and keep specific stability and specific uniqueness. Concretely, the first condition is that the minimum unit cluster is stable as one molecule. The second condition is that the minimum unit cluster keeps its properties at a certain level even after the minimum unit clusters are linked together to form a supercluster.

A supercluster is expected as a novel substance or material that expresses peculiar properties, similar to ordinary clusters. Thus, a technique of producing a supercluster stably and efficiently is extremely valuable in various industrial fields. However, it has been very rare to produce a supercluster actually except for $C_{60}$ polymer (which is one of fullerenes) or the like. There has been the strong need to develop novel superclusters.

As described above, the carborane is a highly stable cluster with a geometrically- and electronically-closed shell. In other words, the carborane forms a cluster molecule. The properties of the carborane molecule are generally defined by the regular-icosahedron-shaped skeletal structure of the carborane itself. It is expected that the carborane molecule keeps its uniqueness even after it is used to form a supercluster, if the carborane molecules are linked together by dehydrogenating condensation (i.e., through hydrogen elimination of the carborane, which applies a small effect to the electron structure) while keeping the skeletal structure of the carborane unchanged.

In this way, although the carborane satisfies the conditions as the constituent unit of a supercluster, there has been no technique for realizing a carborane supercluster under the existing conditions. As a result, it is said that no supercluster consisting of the carborane has been developed so far.

SUMMARY OF THE INVENTION

Accordingly, an object of the present invention is to provide a carborane supercluster consisting of carborane ($C_2B_{10}H_{12}$) as its constituent unit (i.e., a cluster or molecule) and a method of producing the same.

Another object of the present invention is to provide a carborane supercluster consisting of carborane ($C_2B_{10}H_{12}$) as its constituent unit, the structure of which is controllable on an atomic-size (i.e., nanometer) scale, and a method of producing the same.

The above objects together with others not specifically mentioned will become clear to those skilled in the art from the following description.

According to the first aspect of the invention, a carborane supercluster is provided. This carborane supercluster consists essentially of linked clusters of carborane ($C_2B_{10}H_{12}$), where the cluster serves as a constituent unit of the supercluster. This carborane supercluster provides novel substances that have never been reported so far, which is expressed as a molecular formula $C_{2m}B_{10m}H_{12m-x}$, where x is a positive integer (i.e., x=1, 2, 3, . . . ) and m is an integer greater than unity (i.e., m=2, 3, . . . ).

The parameter x represents the count of removed or detached hydrogen atoms. The parameter m represents the count of the clusters linked together. For example, if m=2, the supercluster will be a dimer of the cluster. If m=4, the supercluster will be a tetramer of the cluster.

With the carborane supercluster according to the first aspect of the invention, the cluster or molecule of the highly thermodynamically and chemically stable carborane ($C_2B_{10}H_{12}$) serves as a constituent unit of the supercluster of the invention. Therefore, the carborane supercluster of the invention is applicable to various industrial fields. For example, it is applicable to heat- or fire-resistant materials, chemical-resistant materials, semiconductor materials, neutron capturing materials in the nuclear power plants, medicaments for boron-neutron capture therapy, materials or agents for processing the nuclear waste, and optical components or materials, and their intermediates.

Moreover, the carborane supercluster of the invention is constituted by the cluster or molecule of the highly thermodynamically and chemically stable carborane ($C_2B_{10}H_{12}$). Thus, the structure of the supercluster is controllable on an atomic-size (i.e., nanometer) scale. This means that the supercluster of the invention is applicable to ultrasmall, precision parts or components having specific atomic arrangements in a variety of future industrial fields such as chemical and electronic industries.

Preferably, the cluster of the carborane consists of o-carborane. Alternately, the cluster of the carborane consists of m-carborane or p-carborane. The cluster of the carborane may consist of at least two of o-carborane, m-carborane, and p-carborane.

Preferably, the count of the linked clusters is set at five or thirteen.

According to the second aspect of the invention, a method of producing a carborane supercluster is provided. In this method, carborane ($C_2B_{10}H_{12}$) is ionized to generate carborane ions. Then, the carborane ions thus generated are successively reacted with neutral (i.e., non-ionized) carborane ($C_2B_{10}H_{12}$), thereby generating the supercluster expressed by $C_{2m}B_{10m}H_{12m-x}$ having a cluster structure of the carborane ($C_2B_{10}H_{12}$).

With the method of the second aspect, the supercluster according to the first aspect of the invention is produced.

According to the third aspect of the invention, another method of producing a carborane supercluster is provided. In this method, carborane ($C_2B_{10}H_{12}$) ions are electrically confined in a specific region. Then, the carborane ions thus confined are successively reacted with neutral (i.e., non-ionized) carborane ($C_2B_{10}H_{12}$), thereby generating the supercluster expressed by $C_{2m}B_{10m}H_{12m-x}$ having a cluster structure of the carborane ($C_2B_{10}H_{12}$).

With the method of the third aspect, the supercluster according to the first aspect of the invention is produced.

Even if neutral (i.e., non-ionized) carborane ($C_2B_{10}H_{12}$) is successively reacted with each other in solid or liquid phase, the supercluster expressed by $C_{2m}B_{10m}H_{12m-x}$ according to the first aspect of the invention is unable to be produced. To produce the supercluster of the first aspect, neutral (i.e., non-ionized) carborane ($C_2B_{10}H_{12}$) needs to be successively reacted with the ionized carborane (i.e., carborane ions) in gas phase.

BRIEF DESCRIPTION OF THE DRAWINGS

In order that the present invention may be readily carried into effect, it will now be described with reference to the accompanying drawings.

FIG. 1(a) to FIG. 1(d) show schematically the molecular structures of decaborane (14), o-carborane, m-carborane, and p-carborane, respectively.

DETAILED DESCRIPTION OF THE INVENTION

Figure 2:
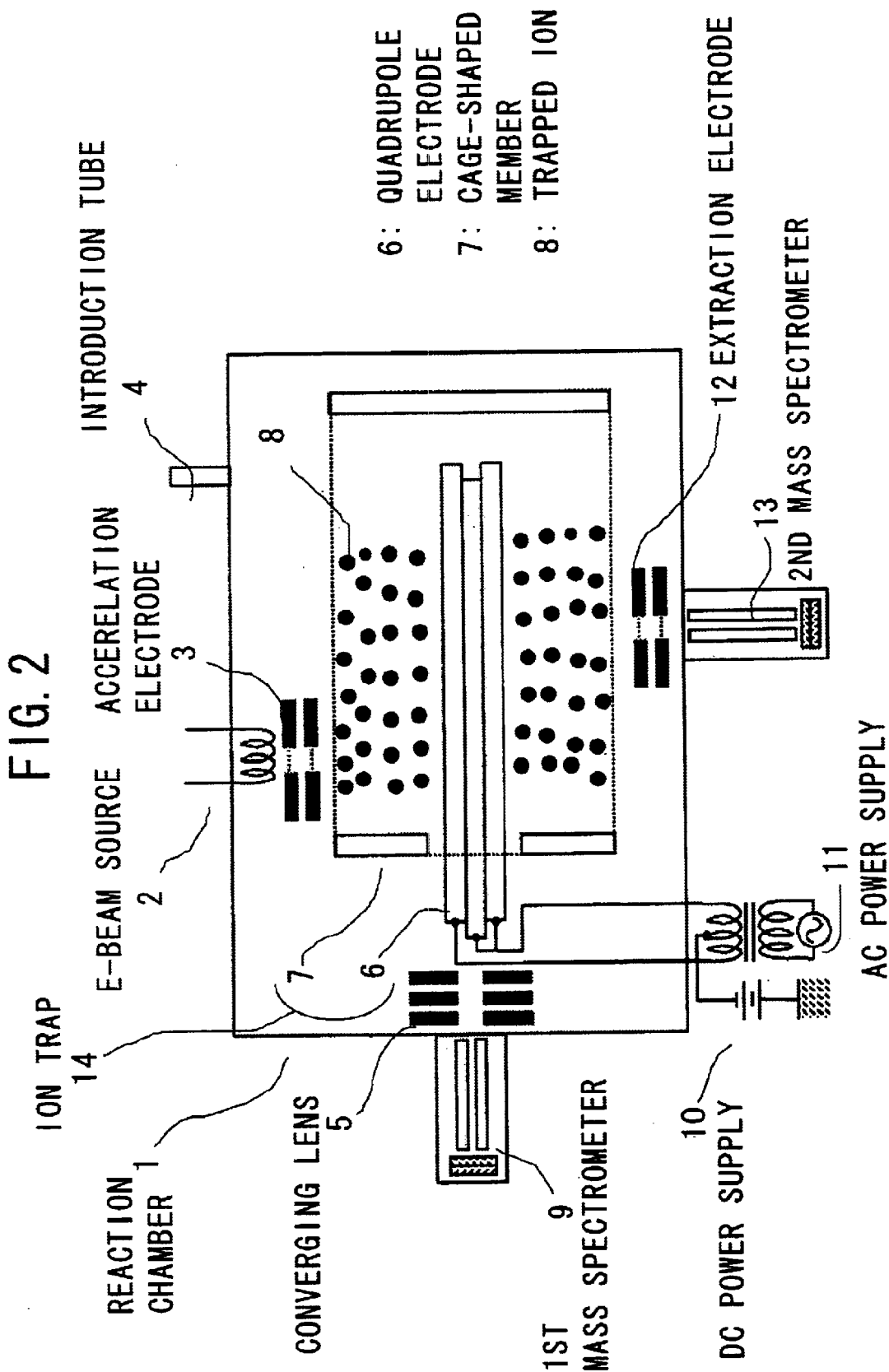
FIG. 2 is a schematic diagram showing the configuration of an apparatus for producing the carborane supercluster according to the invention, where the apparatus has an ion trap.

In the invention, gaseous carborane ($C_2B_{10}H_{12}$) is used as the source material of the carborane supercluster expressed by $C_{2m}B_{10m}H_{12m-x}$ of the invention.

Gaseous carborane ($C_2B_{10}H_{12}$) is filled in a reaction chamber and then, it is subjected to an ion cluster reaction at a room temperature or temperatures, thereby producing a desired carborane supercluster ($C_{2m}B_{10m}H_{12m-x}$). If part of the gaseous carborane is ionized in order to start the reaction, the carborane ions ($C_2B_{10}H_{12}^+$) thus generated and the neutral (i.e., non-ionized) carborane ($C_2B_{10}H_{12}$) are successively reacted with each other, resulting in growth of carborane clusters. On the respective stages of the successive reaction, the carborane molecules are linked together by way of B—B, B–C, or C—C bonds, in which the hydrogen atoms that terminate the boron and carbon atoms are eliminated or removed in the form of hydrogen molecules ($H_2$). This means that the carborane molecules are linked together and grown by way of dehydrogenating condensation.

In the respective stages of the growth of the cluster or molecule, the supercluster is charged. Therefore, the supercluster in the various growth stages can be taken out of the reaction chamber by using a static electric field. Moreover, if the cluster growth is carried out in a reaction chamber with an EQSIT-type ion trap (which is explained later), the supercluster in the various growth stages can be separated from each other by using the transportation function of the ion trap and then, taken out of the reaction chamber in the form of ion beam.

Concrete examples of the carborane supercluster according to the invention are explained below while referring to the drawings attached.

EXAMPLE 1

FIG. 2 shows schematically an apparatus for producing the carborane supercluster of the invention. As shown in FIG. 2, this apparatus comprises a reaction chamber 1 having an airtight structure capable of keeping a desired vacuum condition therein, and a vacuum pump (not shown) to realize desired vacuum conditions in the chamber 1. The apparatus further comprises an electron-beam (e-beam) source 2, an acceleration electrode 3, a gas introduction tube 4, a converging lens 5, a quadrupole electrode 6, a cage-shaped metal member 7, a first mass spectrometer 9, a direct-current (dc) power supply 10, an alternate-current (ac) power supply 11, an extraction electrode 12, and a second mass spectrometer 13. The quadrupole electrode 6 and the cage-shaped metal member 7 constitute an ion trap 14 of the type of EQSIT (External Quadrupole Static attraction Ion Trap). The trap 14 is located in the chamber 1. The acceleration electrode 3, the converging lens 5, and the extraction electrode 12 are located in the chamber 1 as well.

The e-beam source 2, which comprises a tungsten (W) filament, is used to generate an electron beam in the chamber 1. The acceleration electrode 3, which is located near the source 2 in the chamber 1, is used to accelerate the e-beam thus generated with a static electric field. The e-beam thus accelerated is irradiated toward the ion trap 14, thereby ionizing the atoms or molecules or clusters existing in the trap 14. The e-beam is irradiated to be perpendicular to the axis of the trap 14.

The gas introduction tube 4 is used for introducing gaseous carborane as the source material of the desired carborane supercluster into the chamber 1. If necessary, an appropriate relaxation gas (e.g., an inert gas such as helium) is additionally introduced into the chamber 1. The relaxation gas is introduced by way of the tube 4 as well.

The converging lens 5 is located in the chamber 1 near the inlet of the first mass spectrometer 9. The lens 5 is used for converging the flow of the ions 8 generated and trapped in the trap 14 before the ions 8 are introduced into the spectrometer 9.

The ion trap 14 is constituted by the quadrupole electrode 6 and the cylindrical cage-shaped, metal member 7 that surrounds the electrode 6. The trap 14 is used to trap desired ions 8 in a specific region temporarily in the chamber 1. The electrode 6 is electrically connected to the dc power supply 10 and the ac power supply 11, where both power supplies 10 and 11 are located outside the chamber 1. A proper dc voltage and a proper ac voltage are simultaneously applied across the electrode 6 and the member 7 to generate an electrical trapping potential between the center of the electrode 6 and the periphery of the member 7 along the radius of the trap 14. The trapping potential thus generated is used to trap or capture the ions 8 and sustain the same in the trap 14 for reaction. The ions 8 thus trapped can be coaxially transported to the outside of the trap 14 toward the converging lens 5.

The detailed structure of the device 14 is disclosed in the Japanese Non-Examined Patent Publication No. 9-61597 published in 1997, the contents of which are hereby incorporated by reference.

The extraction electrode 12 is provided in the chamber 1 near the inlet of the second mass spectrometer 13. The electrode 12 is used for extracting the ions 8 generated and trapped in the trap 14 before the ions 8 are introduced into the spectrometer 13. Therefore, the ions 8 thus trapped can be radially transported to the outside of the trap 14 toward the electrode 12.

The first and second mass spectrometers 9 and 13 are used for observing or checking the cluster growth based on the ions 8 transported from the ion trap 14 by way of the converging lens 5 and the extraction electrode 12, respectively.

The first and second mass spectrometers 9 and 14 and the mechanism for trapping, sustaining, and transporting the ions are not essential for producing the desired supercluster. Therefore, they may be omitted. Needless to say, they may have any other structures than those used in the apparatus of FIG. 2.

The carborane ions and the carborane supercluster ions in their growth process, are generated and trapped for a specific period in the ion trap 14. The carborane supercluster ions thus produced are taken out of the trap 14 in one of the following two manners.

The first manner is that the supercluster ions are transported through the inner space of the electrode 6 while mass-separating the same. This method is used in the case where the supercluster ions existing in their various growth stages are continuously taken out of the trap 14 while continuously irradiating an e-beam. The mass analysis is conducted with the first mass spectrometer 9.

The second manner is that the supercluster ions are forcibly taken out of the trap 14 with the use of static electric field. This method is used in the case where the reaction of the carborane supercluster ions with the remaining neutral carborane is started with a pulsed e-beam and then, the supercluster ions existing in their various growth stages are instantaneously taken out of the trap 14 after a specific reaction period. The mass analysis is conducted with the second mass spectrometer 13.

Using the apparatus of FIG. 2, the desired carborane supercluster ($C_{2m}B_{10m}H_{12m-x}$) was produced in the following way. Here, a gaseous o-carborane (o-$C_2B_{10}H_{12}$) (purity; 99.9%) was used as the source material.

First, a desired vacuum condition was created in the reaction chamber 1 where no degassing will occur from the inner walls of the chamber 1.

Next, a gaseous o-carborane (o-$C_2B_{10}H_{12}$) (purity: 99.9%) as the source material was introduced into the chamber 1 by way of the gas introduction tube 4. The gas pressure of the o-carborane thus introduced was set at $1.0 \times 10^{-6}$. As a relaxation gas, for example, helium (He) gas may be introduced into the chamber 1 along with the carborane by way of the inlet 4. The temperature of the chamber 1 was kept at room temperatures.

Thereafter, an e-beam was generated by the e-beam source 2, where the emission current was set at 0.10 mA. Due to irradiation of the e-beam thus generated, the molecules of o-carborane were partially ionized, in other words, c-carborane ions (o-$C_2B_{10}H_{12}^+$) were generated in the chamber 1. At this time, o-carborane ions (o-$C_2B_{10}H_{12}^+$) and non-ionized (i.e., neutral) o-carborane molecules (o-$C_2B_{10}H_{12}$) were present in the chamber 1. The o-carborane ions (o-$C_2B_{10}H_{12}^+$) started a reaction with the remaining, neutral o-carborane molecules (o-$C_2B_{10}H_{12}$) in the chamber 1, resulting in growth of o-carborane supercluster (o-$C_{2m}B_{10m}H_{12m-x}$).

The o-carborane supercluster (o-$C_{2m}B_{10m}H_{12m-x}$) thus generated was taken out of the ion trap 14 by the above-described second manner.

Figure 3:
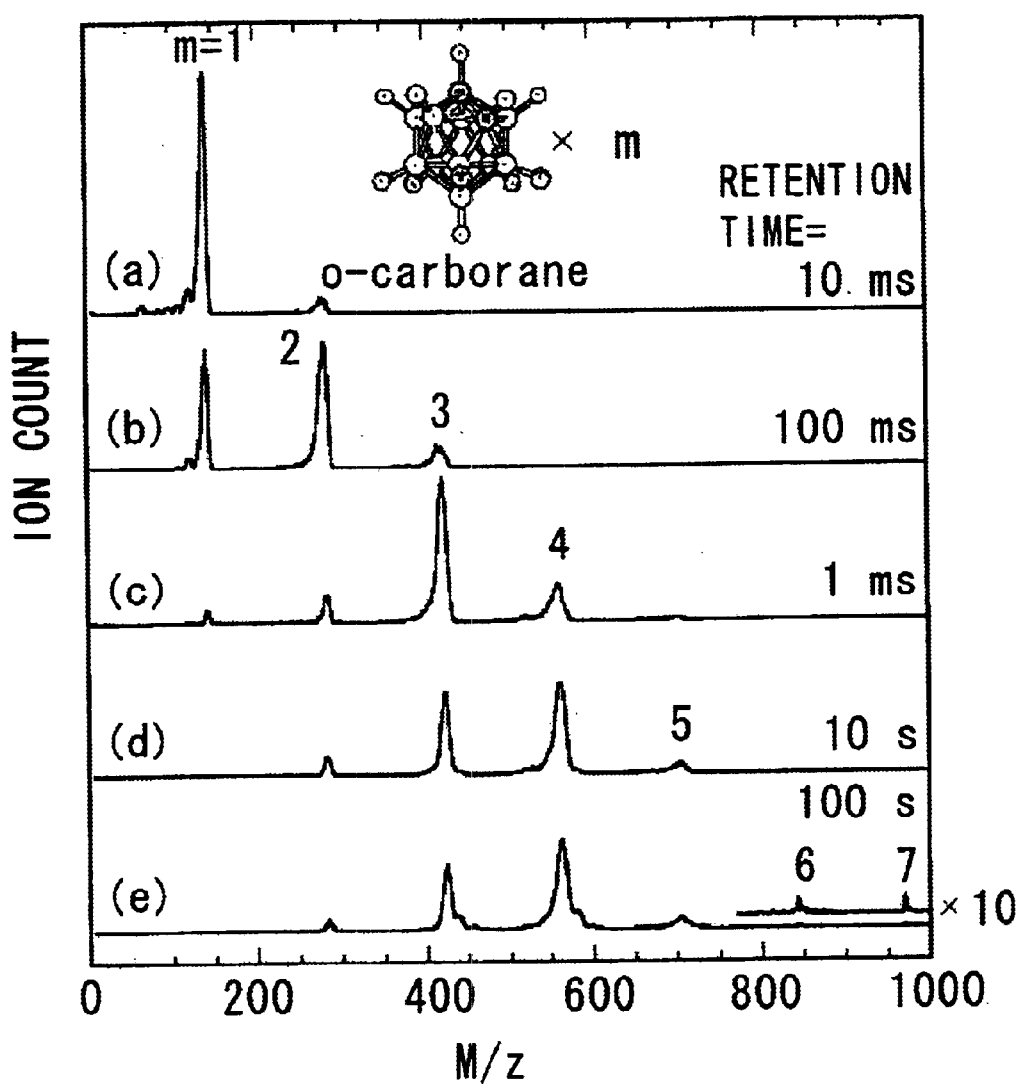
FIG. 3 is a graph showing time-resolved quadrupole mass spectra that represent the growth situation of the carborane supercluster according to the invention, which is constituted by o-carborane.

FIG. 3 shows a time-resolved quadrupole mass spectrum that represents the growth of the o-carborane supercluster (o-$C_{2m}B_{10m}H_{12m-x}$) according to the invention. The lateral axis denotes the ratio of mass M to electrical charge z (unit: amu (atomic mass unit)) while the vertical axis denotes the ion count observed.

As seen from FIG. 3(a), when the retention time of the o-carborane ions (o-$C_2B_{10m}H_{12}^+$) was 10 ms immediately after the irradiation of the e-beam, a peak corresponding to the monomer ion of the o-carborane (o-$C_{2m}B_{10m}H_{12m-x}$, m=1) was observed at M/z=approximately 144. At the same time, another peak corresponding to the start of growth of the dimer ion of the o-carborane supercluster (o-$C_{2m}B_{10m}H_{12m-x}$, m=2) was observed at M/z= approximately 286.

In FIG. 3(b), which shows the state when the retention time of the o-carborane ions (o-$C_2B_{10}H_{12}^+$) was 100 ms after the irradiation of the e-beam, the intensity of the peak corresponding to the monomer ion (o-$C_2B_{10}H_{12}^+$) attenuated slightly and the intensity of the peak corresponding to the dimer ion (i.e., carborane supercluster ion, o-$C_{2m}B_{10m}H_{12m-x}^+$, m=2) increased. At this time, another peak corresponding to the start of growth of the trimer ion (i.e., carborane supercluster ion, o-$C_{2m}B_{10m}H_{12m-x}^+$, m=3) was observed at M/z=approximately 425.

In FIG. 3(c), which, shows the state when the retention time of the o-carborane ions (o-$C_2B_{10}H_{12}^+$) was 1 s after the irradiation of the e-beam, the intensity of the peak corresponding to the dimer ion (i.e., carborane supercluster ion, o-$C_{2m}B_{10m}H_{12m-x}^+$, m=2) almost disappeared. Instead, the intensity of the peak corresponding to the trimer ion (i.e., carborane supercluster ion ion, o-$C_{2m}B_{10m}H_{12m-x}^+$, m=3) became dominant. At this time, another peak corresponding to the start of growth of the tetramer ion (i.e., carborane supercluster ion, o-$C_{2m}B_{10m}H_{12m-x}^+$, m=4) was observed at M/z approximately 560.

The tetramer ion is generally longer in lifetime than the trimer ion or lower. Therefore, it was found that the tetramer ion (i.e., carborane supercluster ion, o-$C_{2m}B_{10m}H_{12m-x}^+$, m=4) was particularly stable. It was supposed that the stability of the tetramer (o-$C_{2m}B_{10m}H_{12m-x}$, m=4) is originated from its structure. Specifically, as explained later, four o-carborane molecules are located at the respective vertexes of a regular tetrahedron and linked together, thereby forming a very firm structure.

In FIG. 3(d), which shows the state when the retention time of the o-carborane ions (o-$C_2B_{10}H_{12}^+$) was 10 s after the irradiation of the e-beam, a peak corresponding to the start of growth of the pentameter ion (i.e., carborane supercluster ion, o-$C_{2m}B_{10m}H_{12m-x}^+$, m=5) was observed at M/z= approximately 735.

In FIG. 3(e), which shows the state when the retention time of the o-carborane ions (o-$C_2B_{10}H_{12}^+$) was 100 s after the irradiation of the e-beam, a peak corresponding to the start of growth of the hexamer ion (i.e., carborane supercluster ion, o-$C_{2m}B_{10m}H_{12m-x}^+$, m=6) was observed at M/z= approximately 840, and another peak corresponding to the start of growth of the heptamer ion (i.e., carborane supercluster ion, o-$C_{2m}B_{10m}H_{12m-x}^+$, m=7) was observed at, M/z= approximately 970.

In the same way as above, the reaction continues and then, the multimers ions of (i.e., carborane supercluster ions, o-$C_{2m}B_{10m}H_{12m-x}^+$, m=8, 9, . . . ) were successively generated and observed.

The above-described mechanism of the growth of the multimers ions or the superclusters (o-$C_{2m}B_{10m}H_{12m-x}^+$) was identified as a cluster growth mechanism based on the ion molecular reaction.

Specifically, first, the monomer ions of the o-carborane (o-$C_2B_{10}H_{12}$) are reacted with the remaining non-ionized molecules of the o-carborane, resulting in the dimer ions of the o-carborane. Next, the dimer ions of the o-carborane are reacted with the remaining, non-ionized molecules o-carborane, resulting in the trimer ions of the o-carborane. Thereafter, the trimer ions of the o-carborane are reacted with the remaining, non-ionized molecules o-carborane, resulting in the tetramer ions of the o-carborane. . . . In the same way, the monomer and multimer ions react successively with the non-ionized, neutral molecules of the o-carborane, resulting in the superclusters of the o-carborane.

Next, what atoms are eliminated or removed during the generation or growth of the carborane supercluster is explained below.

As explained previously, the molecule of carborane ($C_2B_{10}H_{12}$) has a geometrically-closed structure and electronically-closed shell and therefore, it is very firm and stable. Thus, when carborane is in its cluster growth process, in other words, the carborane molecules are linked or coupled together to form the carborane supercluster, the hydrogen atoms surrounding the skeletal carborane structure are eliminated or removed therefrom while keeping this structure unchanged. This was confirmed by the inventors.

Specifically, as shown in FIG. 3, the mass analysis spectra are very simple and thus, they show the fact that no fragmentation accompanying elimination of carbon (C) and/ or boron (B) atoms occurred in the supercluster growth process. This means that the skeletal carborane structure was maintained even after this process. On the other hand, the count of the hydrogen (H) atoms eliminated can be estimated by mass spectra shown in FIGS. 4A and 4B.

Figure 4A:
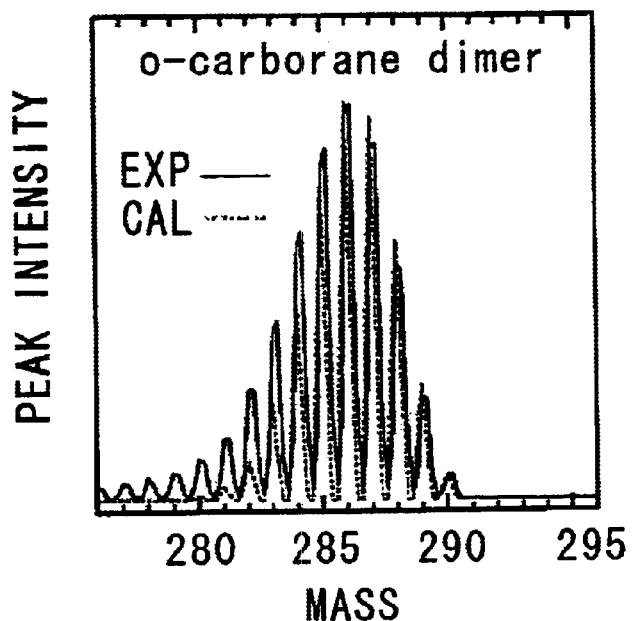
FIG. 4A is a graph showing time-resolved quadrupole mass spectra of o-carborane dimmer, where the solid line denotes the measured spectrum while the broken lines denotes the calculated one.

FIG. 4A shows the high-resolution mass spectra of the dimer ion of the o-carborane supercluster (o-$C_{2m}B_{10m}H_{12m-x}$, m=2), where the solid line denotes the measured one, and the broken line denotes the calculated one obtained under the supposition that two o-carborane molecules are linked together to form the carborane supercluster while eliminating two hydrogen atoms.

Figure 4B:
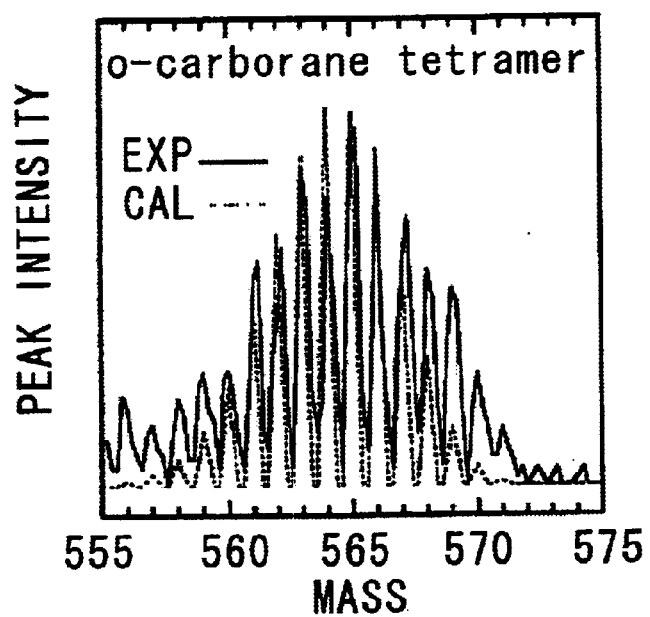
FIG. 4B is a graph showing time-resolved quadrupole mass spectra of o-carborane tetramer, where the solid line denotes the measured spectrum while the broken lines denotes the calculated one.

FIG. 4B shows the high-resolution mass spectra of the tetramer ion of the o-carborane supercluster (o-$C_{2m}B_{10m}H_{12m-x}$, m=4), where the solid line denotes the measured one, and the broken line denotes the calculated one obtained under the supposition that four o-carborane molecules are linked together to form the carborane supercluster while eliminating twelve hydrogen atoms.

As seen from FIGS. 4 and 4B, the calculated spectra accord well with the measured ones, respectively. Accordingly, the following result is given. Specifically, when two o-carborane molecules are linked together to form a carborane supercluster (i.e., a dimer), two hydrogen atoms are eliminated from the skeletal structure of o-carborane. Moreover, when four o-carborane molecules are linked together to form a carborane supercluster (i.e., a tetramer), twelve hydrogen atoms are eliminated from the skeletal structure of o-carborane.

From similar measurement and calculation as above, the following was found. Specifically, when three o-carborane molecules are linked together to form a carborane supercluster (i.e., a trimer), (8±2) (=10 or 6) hydrogen atoms are eliminated from the skeletal structure of o-carborane. When five o-carborane molecules are linked together to form a carborane supercluster (i.e., a pentameter) (16±2) hydrogen atoms are eliminated from the skeletal structure of o-carborane.

The result of the above measurement and calculation is summarized in the following Table 1 that lists the count of hydrogen atoms eliminated.

TABLE 1

|  | MONO-MER | DI-MER | TRI-MER | TETRA-MER | PENTA-MER |
| --- | --- | --- | --- | --- | --- |
| MEASURED VALUE | 0 | 2 | 8 ± 2 | 12 ± 2 | 16 ± 2 |
| CALCULATED | 0 | 4 | 8 | 12 | 16 |

TABLE 1-continued

|  | MONO-MER | DI-MER | TRI-MER | TETRA-MER | PENTA-MER |
|---|---|---|---|---|---|
| VALUE (1-DIM.) CALCULATED VALUE (3-DIM.) | 0 | 2 | 6 | 12 | 18 |

Subsequently, the link state of the o-carborane molecules in the o-carborane supercluster according to the invention is considered.

It was considered that the o-carborane supercluster produced in this example was formed by the o-carborane molecules linked with covalent bonds by way of the B—B, B—C, or C—C bond. Judging from the above-described, count of the eliminated hydrogen atoms, the o-carborane superclusters (m=2, 3, 4, . . .) produced in this example was constituted with the use of the one-dimensional chain link of FIG. 5A or the three-dimensional close-packed link of FIG. 5B.

Figure 5A:
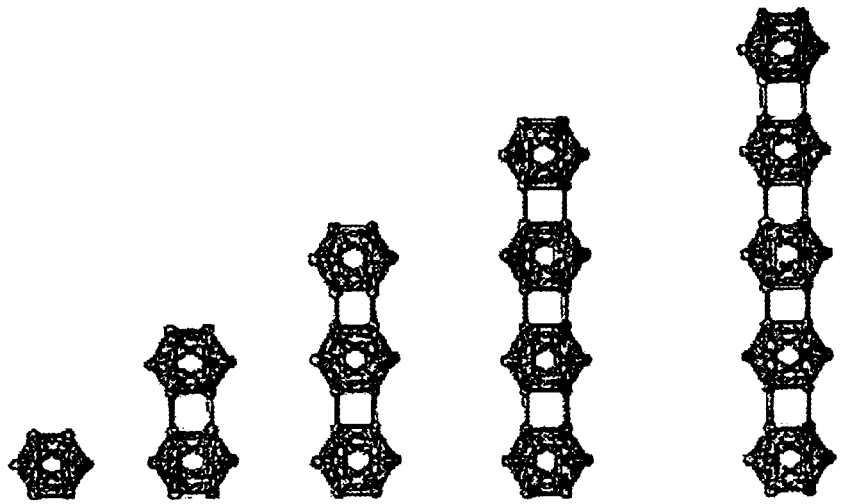
FIG. 5A is a schematic diagram showing the states of the one-dimensional chain link of the carborane cluster.
Figure 5B:
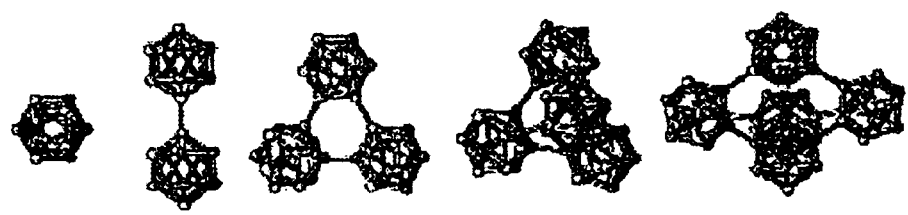
FIG. 5B is a schematic diagram showing the states of the three-dimensional close-packed link of the carborane cluster.

If it was supposed that each of the o-carborane superclusters contains the link of FIG. 5A or FIG. 5B, the count of the eliminated hydrogen atoms was calculated as the respective numbers shown in Table 1. The calculated values are approximately equal to the measured values, respectively, except for the case of the dimer (m=2).

Moreover, if the supercluster has the linear link of FIG. 5A, it will have high strain energy. Since the link of FIG. 4 is simple, there is no reason that the tetramer (m=4) is particularly highly stable. On the other hand, if the supercluster has the three-dimensional link of FIG. 5B, the tetramer (m=4) may be made particularly highly stable. This is because if the tetramer has a regular tetrahedron structure where the centers of the four carborane molecules are located at the respective vertexes of the tetrahedron, it is highly firm in structure and particularly highly stable.

Because of the reason as described above, there is higher possibility that the o-carborane superclusters according to the invention have the three-dimensional link of FIG. 5B.

Figure 6:
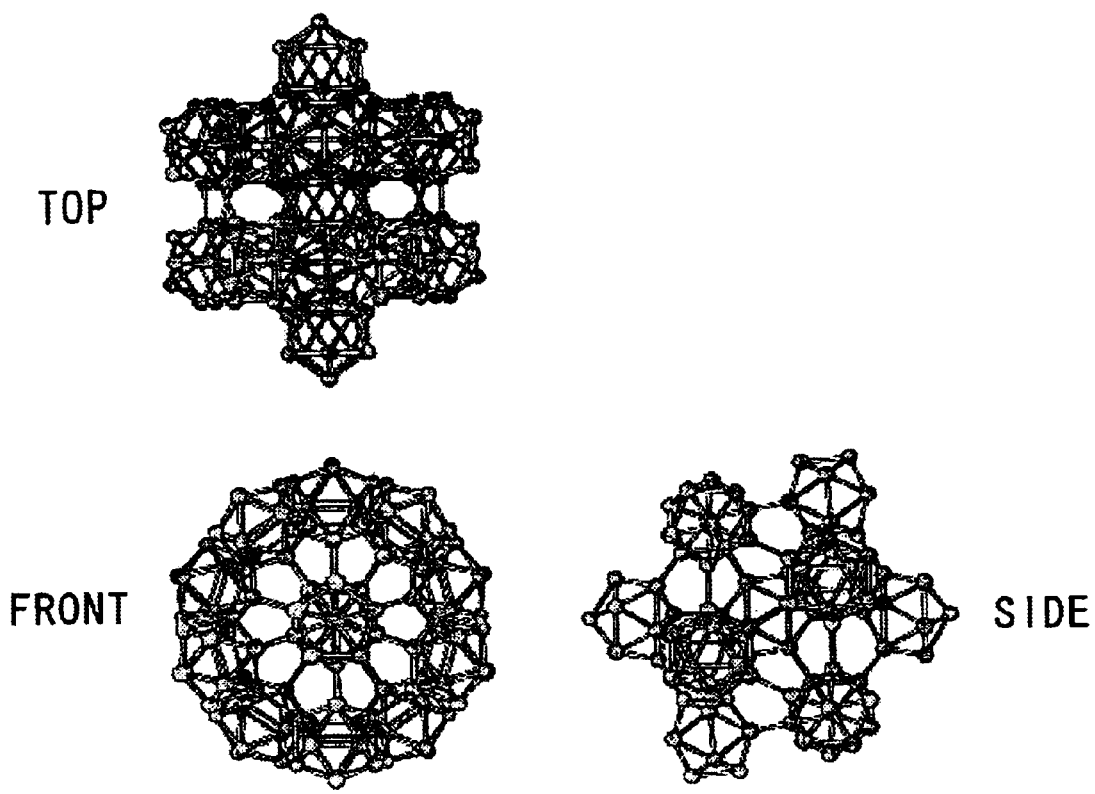
FIG. 6 is a schematic diagram showing schematically the front, top, and side views of the carborane supercluster according to the invention, which has 13 regular-icosahedron-shaped carborane molecules.

If 13 o-carborane molecules are linked together according to the link manner of FIG. 5B, an o-carborane supercluster with the regular icosahedron structure shown in FIG. 6 is constituted, where 12 o-carborane molecules are located at the respective vertexes of a regular icosahedron and the remaining one molecule is at the center thereof. This tridecamer supercluster (m=13) is expected to be firmer in structure and more highly stable in properties than the tetramer supercluster (m=4). This is because the tridecamer supercluster consists of the carborane molecules having the stable and firm structure as its constituent unit and at the same time, the carborane molecules are linked together with many covalent bonds in a close-packed manner.

The tridecamer supercluster (m=13) of FIG. 6 contains 130 boron atoms and 26 carbon atoms excluding the hydrogen atoms and thus, it contains 156 boron and carbon atoms in total. The skeletal structure of the tridecamer excluding the hydrogen atoms is approximately 1.2 to 1.3 nm. Therefore, this is a huge molecule from the molecular standpoint. Comparing it with bulk solid, it may be considered as an ultrasmall (or nanometer-sized) particle. However, the tridecamer differs decisively from ordinary nanometer-sized particles in the following point.

Specifically, with ordinary nanometer-sized particles, an atom is used as their constituent unit. Therefore, some dispersion is always present among the respective particles. On the other hand, with the tridecamer supercluster of the invention, a carborane cluster is used as its constituent unit. Therefore, the size and count of the clusters are constant and isodisperse. Accordingly, if the tridecamer superclusters are collected or accumulated together to form a larger structure, an orderly or systematic structure can be formed easier than the case of ordinary nanometer-sized particles like atoms or molecules are accumulated to form a crystal structure.

Furthermore, it is expected that a material produced by accumulating the tridecamer superclusters will express distinctive or unique properties originated from its own organization or structure. This is applicable to any other superclusters consisting of more carborane molecules than the tridecamer supercluster.

EXAMPLE 2

Instead of gaseous o-carborane (o-$C_2B_{10}H_{12}$) used in Example 1, gaseous m-carborane (m-$C_2B_{10}H_{12}$) (purity: 99.9%) was used as the source material. m-Carborane (m-$C_2B_{10}H_{12}$) was introduced into the chamber 1 by way of the gas introduction tube 4. The gas pressure of the c-carborane thus introduced was set at $1.0 \times 10^{-6}$ Torr, which was the same as Example 1.

Thereafter, an e-beam was generated by the e-beam source 2, where the emission current was set at 0.05 mA, which was less than Example 1. Due to irradiation of the e-beam thus generated, the molecules of m-carborane were partially ionized, in other words, m-carborane ions (n-$C_2B_{10}H_{12}^+$) were generated in the chamber 1. At this time, m-carborane ions (m-$C_2B_{10}H_{12}^+$) and non-ionized (i.e., neutral) m-carborane molecules (m-$C_2B_{10}H_{12}$) were present in the chamber 1. The m-carborane ions started a reaction with the remaining, neutral m-carborane molecules in the chamber 1, resulting in growth of m-carborane supercluster (m-$C_{2m}B_{10m}H_{12m-x}$).

The m-carborane supercluster (m-$C_{2m}B_{10m}H_{12m-x}$) thus generated was taken out of the ion trap 14 by the above-described first manner.

Figure 7:
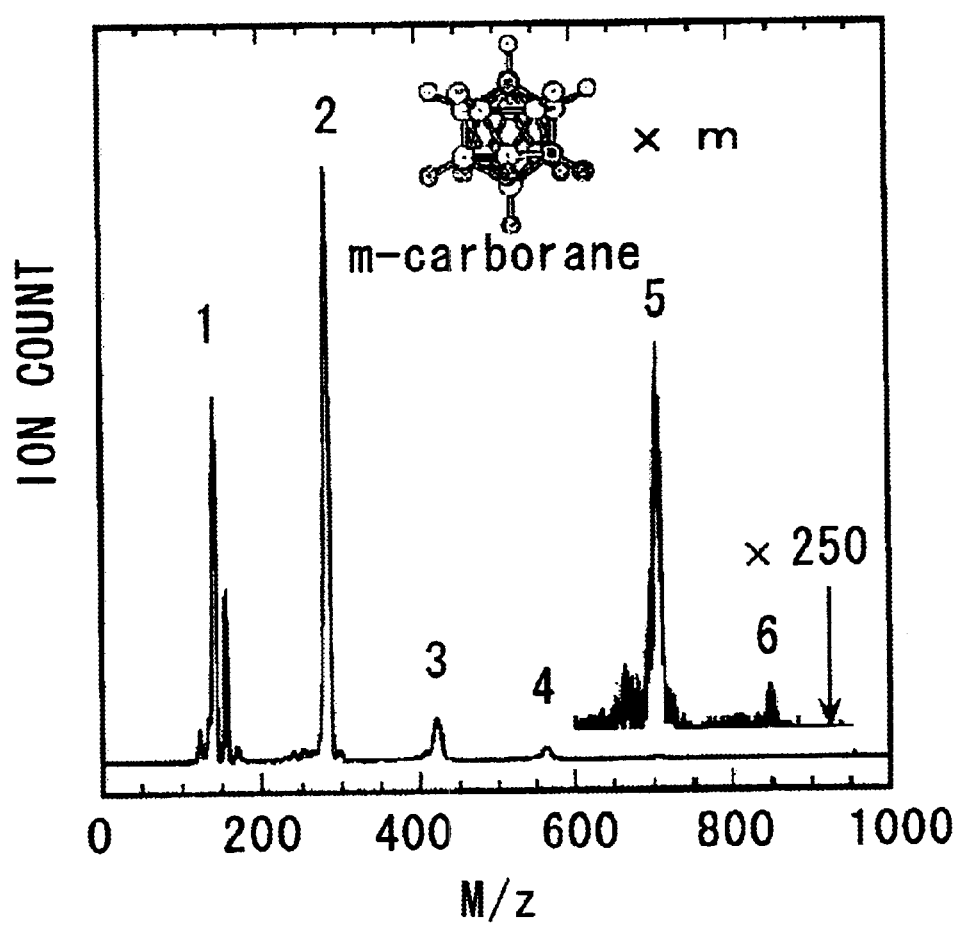
FIG. 7 is a graph showing a quadrupole mass spectrum of m-carborane, which represents the growth of the carborane supercluster according to the invention.

FIG. 7 shows a quadrupole mass spectrum that represents the growth of the m-carborane supercluster (m-$C_{2m}B_{10m}H_{12m-x}$) according to the invention.

As seen from FIG. 7, a first peak corresponding to the monomer ion of the m-carborane (m-$C_{2m}B_{10m}H_{12m-x}$, m=1), and second to sixth peaks corresponding to the multimers of the respective m-carborane superclusters (m-$C_{2m}B_{10m}H_{12m-x}$, m=2, 3, 4, 5, and 6) were observed. This is similar to Example 1.

Accordingly, it was confirmed that the m-carborane superclusters (m-$C_{2m}B_{10m}H_{12m-x}$) were able to be produced from m-carborane.

EXAMPLE 3

Instead of gaseous o-carborane (o-$C_2B_{10}H_{12}$) used in Example 1, gaseous p-carborane (p-$C_2B_{10}H_{12}$) (purity: 99.9%) was used as the source material. p-Carborane (p-$C_2B_{10}H_{12}$) was introduced into the chamber 1 by way of the gas introduction tube 4. The gas pressure of the p-carborane thus introduced was set at $1.0 \times 10^{-6}$ Torr, which was the same as Example 1.

Thereafter, an e-beam was generated by the e-beam source 2, where the emission current was set at 0.05 mA, which was the same as Example 2. Due to irradiation of the e-beam thus generated, the molecules of p-carborane were partially ionized, in other words, p-carborane ions ($p$-$C_2B_{10}H_{12}^+$) were generated in the chamber 1. At this time, the p-carborane ions and non-ionized (i.e., neutral) p-carborane molecules ($p$-$C_2B_{10}H_{12}$) were, present in the chamber 1. The p-carborane ions started a reaction with the remaining, neutral p-carborane molecules in the chamber 1, resulting in growth of p-carborane supercluster ($p$-$C_{2m}B_{10m}H_{12m-x}$).

The p-carborane supercluster ($p$-$C_{2m}B_{10m}H_{12m-x}$) thus generated was taken out of the ion trap 14 by the above-described first manner.

Figure 8:
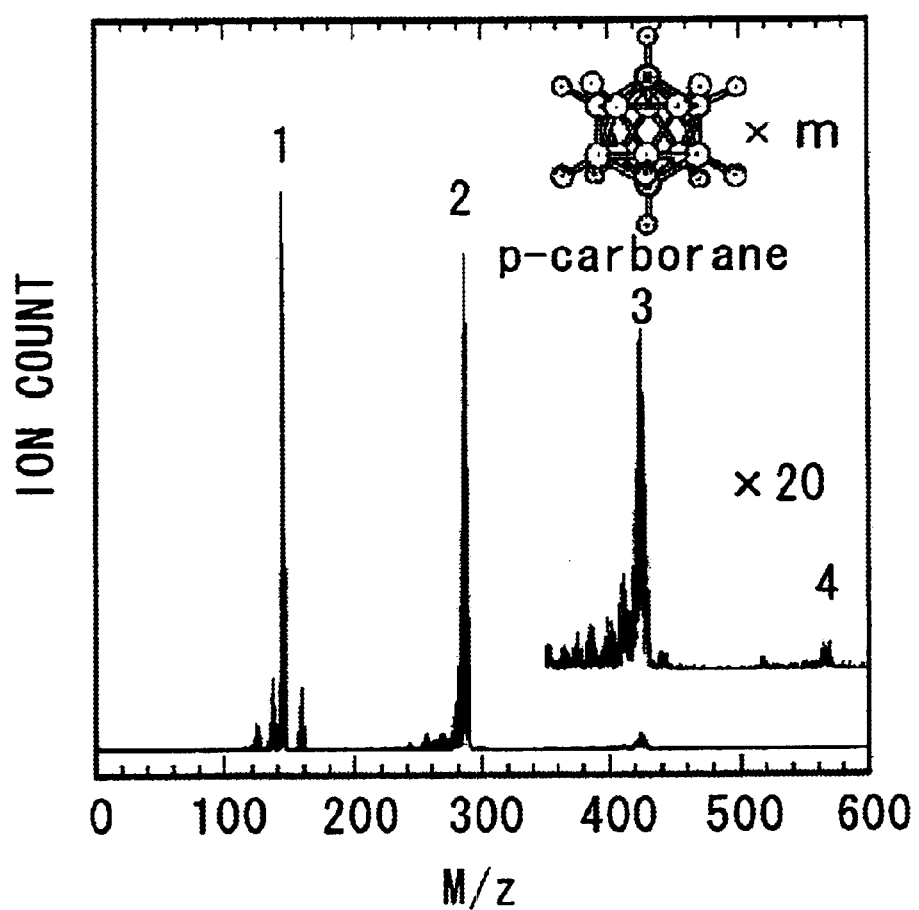
FIG. 8 is a graph showing a quadrupole mass spectrum of p-carborane, which represents the growth of the carborane supercluster according to the invention.

FIG. 8 shows a quadrupole mass spectrum that represents the growth of the p-carborane supercluster ($p$-$C_{2m}B_{10m}H_{12m-x}$) according to the invention.

As seen from FIG. 8, a first peak corresponding to the monomer ion of the p-carborane ($p$-$C_{2m}B_{10m}H_{12m-x}$, m=1), and second to fourth peaks corresponding to the multimers of the respective p-carborane superclusters ($p$-$C_{2m}B_{10m}H_{12m-x}$, m=2, 3, and 4) were observed. This is similar to Example 1.

Accordingly, it was confirmed that the p-carborane superclusters ($p$-$C_{2m}B_{10m}H_{12m-x}$) were able to be produced from p-carborane.

EXAMPLE 4

As the source material, gaseous o-carborane ($o$-$C_2B_{10}H_{12}$) (purity: 99.9%) and gaseous m-carborane ($m$-$C_2B_{10}H_{12}$) (purity: 99.9%) are used. In this case, carborane superclusters each consisting of o-carborane and m-carborane are generated.

EXAMPLE 5

As the source material, gaseous o-carborane ($o$-$C_2B_{10}H_{12}$) (purity. 99.9%) and gaseous p-carborane ($p$-$C_2B_{10}H_{12}$) (purity: 99.9%) are used. In this case, carborane superclusters each consisting of o-carborane and p-carborane are generated.

EXAMPLE 6

As the source material, gaseous m-carborane ($m$-$C_2B_{10}H_{12}$) (purity: 99.9%) and gaseous p-carborane ($p$-$C_2B_{10}H_{12}$) (purity: 99.9%) are used. In this case, carborane superclusters each consisting of n-carborane and p-carborane are generated.

EXAMPLE 7

As the source material, gaseous o-carborane ($o$-$C_2B_{10}H_{12}$) (purity: 99.9%, gaseous m-carborane ($m$-$C_2B_{10}H_{12}$) (purity: 99.9%), and gaseous p-carborane ($p$-$C_2B_{10}H_{12}$) (purity: 99.9%) are used. In this case, carborane superclusters each consisting of o-carborane, m-carborane, and p-carborane are generated.

EXAMPLE 8

As the source material, gaseous p-carborane ($p$-$C_2B_{10}H_{12}$) (purity; 99.9%) was used. The p-carborane was introduced into the reaction chamber 1 of the apparatus of FIG. 2. Helium (He), hydrogen ($H_2$), or deuterium ($D_2$) was introduced into the chamber 1 to generate an atmosphere of He, $H_2$, or $D_2$ in the chamber 1. Thereafter, an e-beam was irradiated to the p-carborane thus introduced in the He, $H_2$, or $D_2$ atmosphere, thereby producing p-carborane ions ($p$-$C_2B_{10}H_{12}^+$). The p-carborane ions thus generated were trapped by the ion trap 14 and then, subjected to mass analysis with the mass spectrometer 9 or 13.

Figure 9:
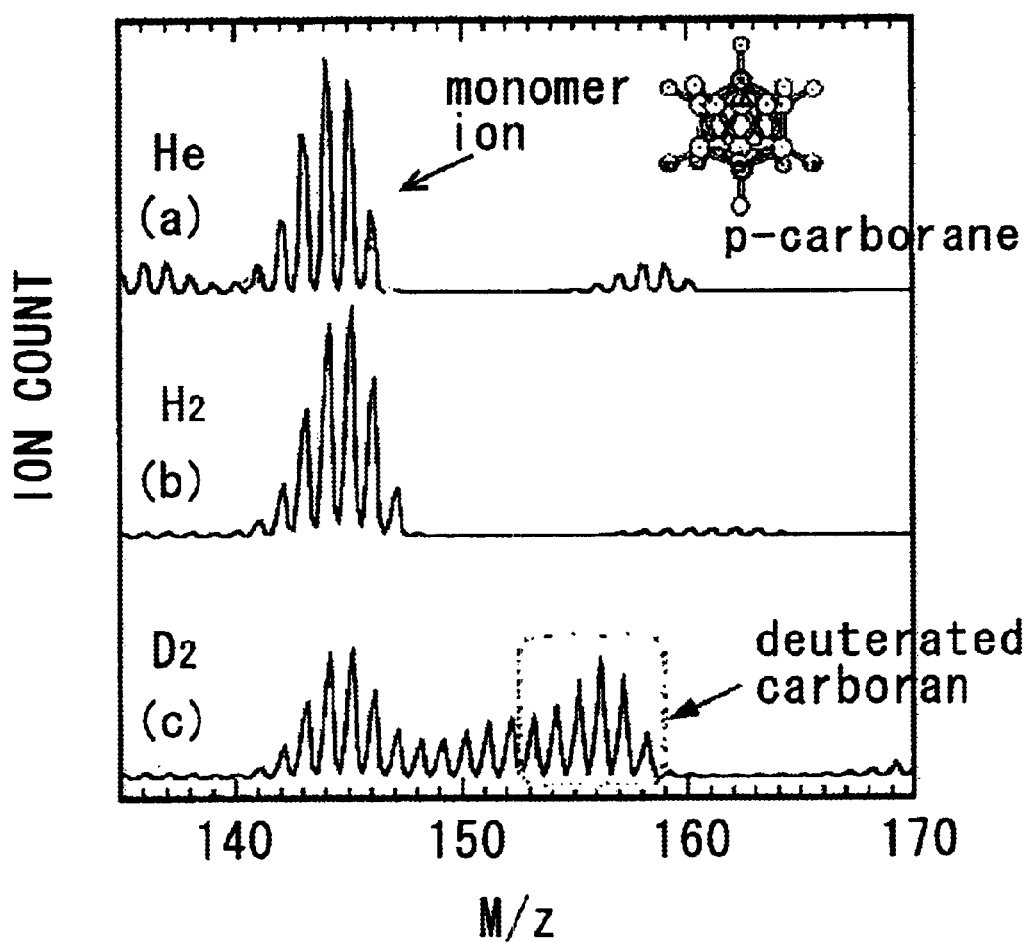
FIG. 9 is a graph showing quadrupole mass spectra of ionized p-carborane, which represents the generation of the carborane supercluster according to the invention in the He, $H_2$ and $D_2$ atmospheres.

FIG. 9 shows the mass spectra of the monomer (m=1) of the p-carborane ion in the He, $H_2$, and $D_2$ atmosphere. A series of peaks observed in the spectrum of FIG. 9(*a*) in the He atmosphere at M/z=141 to 146 corresponds to the p-carborane ion ($p$-$C_2B_{10}H_{12}^+$). In the spectrum of FIG. 9(*b*) in the $H_2$ atmosphere, the series of the peaks are shifted toward the higher mass side (i.e., toward the right side in FIG. 9) by 1 amu (which corresponds to one hydrogen atom).

This change or shift is considered to correspond the change that a hydrogen atom is added to the p-carborane ion ($p$-$C_2B_{10}H_{12}^+$), resulting in ($p$-$C_2B_{10}H_{13}$)$^+$·($p$-$C_2B_{10}H_{12}$)$H^+$. The ($p$-$C_2B_{10}H_{13}$)$^+$ ions and the ($p$-$C_2B_{10}H_{12}$)$H^+$ ions are considered to be in equilibrium. The reason of this can be thought in the following way.

With the non-ionized or neutral p-carborane ($p$-$C_2B_{10}H_{12}$), 26 electrons are inserted into the 13 bonding molecular orbitals in the cage-shaped skeletal structure to close electronically the shell, resulting in high stability. If the neutral p-carborane is ionized, one electron is removed from the structure and the shell is not closed. However, one hydrogen atom is added to the p-carborane ion, the carborane shell gets one electron from the hydrogen atom to close its shell. This means that the ($p$-$C_2B_{10}H_{13}$)$^+$ ions and the ($p$-$C_2B_{10}H_{12}$)$H^+$ ions are stable.

Accordingly, in the atmosphere that allows the p-carborane ions to get electrons, it is considered that the p-carborane ions are likely to remove desired electrons from the hydrogen atoms to become ($p$-$C_2B_{10}H_{13}$)$^+$·($p$-$C_2B_{10}H_{12}$)$H^+$. A similar tendency to this is seen in the atmosphere of silane ($SiH_4$) containing hydrogen atoms. This fact serves as a support for the inventors' thinking.

In the spectrum of FIG. 9(*c*) in the $D_2$ atmosphere, two peaks were observed at M/z=142 to 147 and 153 to 158. This H—D replacement is considered that approximately half of the p-carborane ions ($p$-$C_2B_{10}H_{12}^+$) trapped in the trap 14 were deuterated. This phenomenon was not observed for the non-ionized, neutral p-carborane molecules.

Accordingly, it is supposed that the B—H and C—H bonds of the p-carborane molecules are weakened by ionization; in other words, the hydrogen atoms in the p-carborane molecule have a tendency to leave its skeletal structure and a reaction accompanying the dehydrogenation action is likely to occur. Considering additionally the fact that carborane superclusters are unable to be produced from only non-ionized or neutral carborane molecules, it is the most important thing that carborane ions (i.e., ionized carborane molecules) are generated and thereafter, the carborane ions thus generated are successively reacted with non-ionized carborane molecules.

While the preferred forms of the present invention have been described, it is to be understood that modifications will be apparent to those skilled in the art without departing from the spirit of the invention. The scope of the present invention, therefore, is to be determined solely by the following claims.

What is claimed is:

1. A carborane supercluster consisting of linked clusters of carborane ($C_2B_{10}H_{12}$), where the cluster serves as a constituent unit of the supercluster;

the supercluster being expressed as a molecular formula $C_{2m}B_{10m}H_{12m-x}$, where x is a positive integer greater than m and m is five to thirteen.

2. The supercluster according to claim 1, wherein the carborane is o-carborane.

3. The supercluster according to claim 1, wherein the carborane is m-carborane.

4. The supercluster according to claim 1, wherein the carborane is p-carborane.

5. The supercluster according to claim 1, wherein the carborane is a mixture of at least two of o-carborane, m-carborane, and p-carborane.

6. The supercluster according to claim 1, wherein m is thirteen.

7. A method of producing a carborane supercluster, comprising:

ionizing carborane ($C_2B_{10}H_{12}$) to generate positive carborane ions; and successively reacting the carborane ions with neutral carborane ($C_2B_{10}H_{12}$), thereby generating a supercluster expressed by $C_{2m}B_{10m}H_{12m-x}$ having a cluster structure of the carborane ($C_2B_{10}H_{12}$);

wherein x is a positive integer at least as great as m and m is five to thirteen.

8. The method according to claim 7, wherein the carborane is o-carborane.

9. The method according to claim 7, wherein the carborane is m-carborane.

10. The method according to claim 7, wherein the carborane is p-carborane.

11. The method according to claim 7, wherein the carborane is a mixture of at least two of o-carborane, m-carborane, and p-carborane.

12. The method according to claim 7, wherein m is five or thirteen.

13. A method of producing a carborane supercluster, comprising:

electrically confining positive carborane ($C_2B_{10}H_{12}$) ions in a specific region, and successively reacting the carborane ions with neutral carborane ($C_2B_{10}H_{12}$), thereby generating a supercluster expressed by $C_{2m}B_{10m}H_{12m-x}$ having a cluster structure of the carborane wherein x is a positive integer at least as great as m and m is an five to thirteen.

14. The method according to claim 13, wherein the carborane is o-carborane.

15. The method according to claim 13, wherein the carborane is m-carborane.

16. The method according to claim 13, wherein the carborane is p-carborane.

17. The method according to claim 13, wherein the carborane is a mixture of at least two of o-carborane, m-carborane, and p-carborane.

18. The method according to claim 13, wherein m is five or thirteen.

* * * * *